(12) United States Patent
Ryan (10) Patent No.: US 10,835,646 B2
(45) Date of Patent: Nov. 17, 2020

(54) CHARGED GRAFTS AND METHODS FOR USING THEM

(76) Inventor: Timothy J. Ryan, Cleveland Heights, OH (US)

(*) Notice: Subject to any disclaimer, the term of this patent is extended or adjusted under 35 U.S.C. 154(b) by 0 days.

(21) Appl. No.: 13/431,933

(22) Filed: Mar. 27, 2012

(65) Prior Publication Data
US 2012/0185033 A1 Jul. 19, 2012

Related U.S. Application Data

(63) Continuation of application No. PCT/US2010/050419, filed on Sep. 27, 2010.
(Continued)

(51) Int. Cl.
*A61F 2/06* (2013.01)
*A61F 2/07* (2013.01)
(Continued)

(52) U.S. Cl.
CPC ............ *A61L 33/0005* (2013.01); *A61F 2/06* (2013.01); *A61F 2/07* (2013.01); *A61F 2/2403* (2013.01); *A61L 27/34* (2013.01); *A61L 27/50* (2013.01); *A61L 27/507* (2013.01); *A61L 29/085* (2013.01); *A61L 29/14* (2013.01); *A61M 1/3653* (2013.01); *A61M 1/3659* (2014.02); *A61M 1/3661* (2014.02); *A61N 1/20* (2013.01); *A61N 1/205* (2013.01); *A61F 2/89* (2013.01); *A61F 2002/075* (2013.01); *A61F 2220/0075* (2013.01); *A61M 1/3655* (2013.01)

(58) Field of Classification Search
CPC ...... A61F 2/04; A61F 2/06; A61F 2/07; A61F 2/89; A61F 2250/0001; A61F 2250/0043; A61F 2250/0045; A61L 33/00

USPC ................ 607/2; 623/3.27; 606/32
See application file for complete search history.

(56) References Cited

U.S. PATENT DOCUMENTS 4,906,207 A * 3/1990 Banning et al. .............. 439/578
6,206,914 B1 * 3/2001 Soykan ..................... A61F 2/02
604/891.1

(Continued)

OTHER PUBLICATIONS

The International Bureau of WIPO; International Preliminary Report on Patentability for related application PCT/US2010/050419; Apr. 12, 2012; 6 pages.
(Continued)

*Primary Examiner* — Dinah Baria
(74) *Attorney, Agent, or Firm* — William A. English; Vista IP Law Group LLP (57) ABSTRACT

A system for preventing thrombosis in an implantable medical device includes an implantable medical device sized for implantation at least partially within a patient's body. The device includes an at least partially electrically conductive portion that is disposed within a patient's body upon implantation, an electrode coupled to the electrically conductive portion of the device; and a power source coupled to the electrode. The power source provides a negative electric charge to the at least partially electrically conductive portion for an indefinite period of time. The device may be configured to resist thrombosis, infection, and/or undesired tissue growth via the charged conductive portion once implanted. Exemplary embodiments of the implantable medical device include a hemodialysis vasculature graft, a dialysis catheter, a coronary artery, and a heart valve.

23 Claims, 7 Drawing Sheets

Related U.S. Application Data (60) Provisional application No. 61/246,457, filed on Sep. 28, 2009.

(51) Int. Cl.
*A61F 2/82* (2013.01)
*A61L 33/00* (2006.01)
*A61M 1/36* (2006.01)
*A61L 27/34* (2006.01)
*A61N 1/20* (2006.01)
*A61L 29/14* (2006.01)
*A61F 2/24* (2006.01)
*A61L 27/50* (2006.01)
*A61L 29/08* (2006.01)
*A61F 2/89* (2013.01)

(56) References Cited

U.S. PATENT DOCUMENTS

| | | | | |
|---|---|---|---|---|
| 6,228,845 | B1* | 5/2001 | Donovan | A61F 2/82 |
| | | | | 264/279 |
| 6,648,881 | B2 | 11/2003 | KenKnight et al. | |
| 2006/0009804 | A1* | 1/2006 | Pederson | 607/2 |
| 2006/0106451 | A1* | 5/2006 | Busiashvili | 623/1.15 |
| 2007/0224244 | A1* | 9/2007 | Weber et al. | 424/426 |
| 2008/0288019 | A1* | 11/2008 | Heller | A61K 31/13 |
| | | | | 607/46 |
| 2009/0132009 | A1* | 5/2009 | Torgerson | 607/61 |

OTHER PUBLICATIONS

The International Bureau of WIPO; International Preliminary Report on Patentability for related application PCT/US2006/061667; Jun. 10, 2009; 9 pages.

* cited by examiner

CHARGED GRAFTS AND METHODS FOR USING THEM

RELATED APPLICATION DATA

This application is a continuation of co-pending International Application No. PCT/US2010/050419, filed Sep. 27, 2010, which claims benefit of co-pending provisional application Ser. No. 61/246,457, filed Sep. 28, 2009, the entire disclosures of which are expressly incorporated by reference herein.

FIELD OF THE INVENTION

The present invention relates generally to devices that may be implanted within a patient's body, and, more particularly, to electrically charged implants, e.g., which may reduce susceptibility to infection, thrombosis, and/or undesired tissue growth, and to apparatus and methods for making and using them.

BACKGROUND

Two common problems with implanted devices are infection and thrombosis. Microbes adhere to foreign material and often form a biofilm. This biofilm is relatively resistant to attack by immune molecules and cells, and also relatively impermeable to therapeutic levels of antibiotics and other drugs. Accordingly, an implant, whether it is a simple intravenous catheter, a heart valve, a vascular graft, or a total hip prosthesis, once infected, often must be removed to achieve clearance of the infection. The device, if still needed, is then replaced after the infection is cleared.

In addition, another shortcoming of many prosthetic vascular graft material, valves, and catheters is the propensity of blood to clot when in contact with foreign material. Depending on the location and criticality of the application, various solutions have been proposed to limit such clotting. In the setting of a mechanical heart valve, for example, systemic blood thinners (e.g., Coumadin or Warfarin) may be given orally to reduce the propensity of clot formation. Such compounds must usually be converted to a shorter-acting injectable drug if a patient is to undergo any invasive procedure. This is generally effective, though with an associated risk of bleeding from what may otherwise be a minor injury. This risk of bleeding, particularly intracranial bleeding, is increased in the elderly who are unfortunately the most likely patients to have an artificial valve or other medical implant.

Catheters, such as for hemodialysis, may be filled with a concentrated solution of heparin in saline. While large diameter vascular grafts typically do not suffer from thrombosis, small diameter grafts may be doomed to failure, in part due to thrombosis for which no other effective, safe prevention has been identified. This has prevented the availability of a prosthetic coronary artery graft, and frequently dooms grafts in the lower leg to failure.

Accordingly, apparatus and methods that may reduce susceptibility to infection, thrombosis, and/or undesired tissue growth often associated with temporarily or permanently implanted devices would be useful.

SUMMARY OF THE INVENTION

The present invention is directed to implantable medical devices, e.g., for reducing and/or preventing thrombosis, infection, and/or undesired tissue growth, and to apparatus and methods for making and using them. For example, the apparatus and methods described herein may limit the ability of microbes to adhere to prosthetic material, e.g., to vascular grafts, valves, and catheters of any type, but may be applicable to almost any medical implant.

The apparatus and methods described herein may be applied to various devices that may be implanted temporarily or substantially permanently within a patient's body, for example, devices in the fields of vascular surgery and/or cardiac surgery, such as vascular grafts, mechanical heart valves, and intravenous or intra-arterial catheters. Such catheters may be intended to remain in place within a patient's body for an extended period of time, for example, dialysis catheters in any anatomic position, peritoneal dialysis catheters, and/or single or multiple lumen catheters, which may be placed in critically ill patients. Such catheters are often referred to by their anatomic locations, e.g., a "subclavian line," "femoral line," and the like.

Most cells have a negative charge on their surface, largely carried by protein and carbohydrate molecules on their surface, collectively sometimes referred to as known as glycocalyx. This is true of red blood cells and platelets, as well as endothelial cells. These negatively charged surfaces reduce the interactions between cells and the vascular walls and contribute to the absence of thrombosis in anatomic vessels. When the endothelium is injured, however, the basement membrane may be exposed, thus attracting and helping to activate platelets. Apparatus and methods described herein may involve applying a slight negative charge to medical implants, e.g., to reduce interaction with negatively charged cells within the body, and to inhibit the intrinsic or extrinsic pathways of the coagulation cascade, for example, to reduce thrombosis, infection, and/or undesired tissue growth.

In accordance with one embodiment, a system is provided for preventing thrombosis in an implantable medical device. The system generally includes an implantable medical device sized for implantation at least partially within a patient's body, the device including an at least partially electrically conductive portion that is exposed within a patient's body upon implantation. For example, the at least partially conductive portion may include an electrically semi-conductive material, or an electrically conductive material covered with a thin layer of semi-conductive or non-conductive material, to limit or otherwise control leakage or other electrical flow from and/or through the conductive portion.

A power source may be coupled to the at least partially conductive portion of the device, e.g., via one or more electrodes, for providing a negative electric charge to the at least partially electrically conductive portion, e.g., for maintaining a slight negative electric charge between about 0 and 0.5 Volts (0-0.5 V) on the at least partially conductive portion. The power source may include a circuit, e.g., an inverting operational amplifier or a voltage divider, coupled to a battery and/or other electrical storage device for providing the negative charge to the at least partially conductive portion. In exemplary embodiments, the device may be a heart valve, a vascular graft, a catheter, an aortic endograft, or other implantable device.

In accordance with another embodiment, a method is provided for preventing thrombosis, infection, and/or undesired tissue growth on an implantable device that includes implanting the device within a patient's body, the device including an at least partially electrically conductive portion. A negative electrical charge is applied to and/or maintained on the conductive portion for an indefinite time, e.g., to prevent cells from adhering to the conductive portion and/or inhibit at least partially the intrinsic and or extrinsic coagulation pathways.

In another embodiment, a urinary bladder catheter may be constructed such that at least a portion of the surface of the catheter is electrically conductive. A power source is connected to the catheter such that the surface of the catheter is electrically charged at least part of the time the catheter is placed in the bladder. By providing an electrical charge on the surface of at least a portion of the catheter, urinary tract infection may be prevented.

Similarly, conductive and charged surfaces may be provided on catheters for peritoneal dialysis catheters. In another embodiment, a nephrostomy tube is constructed with at least a portion of the surface electrically conductive. A power supply is provided to maintain an electrical charge on at least a portion of the catheter.

In yet another embodiment, a central venous catheter is constructed with an electrically conductive surface over at least a portion of the catheter. A source of electrical energy, for example a battery or other power supply, and a lead connecting the battery to the catheter are also provided. A skin electrode connects the circuit from the patient's skin, through the battery, to the lead, and the catheter, which then completes the circuit within the patient.

In accordance with still another embodiment, a fluid conduit is provided that includes a surface, at least a portion of the surface being electrically conductive. Means for applying an electrical charge to the conductive surface may also be provided, e.g., a battery or other power source, coupled to the electrically conductive surface. At least a portion of the conduit may be sized for at least temporary implantation into a human patient. As used herein, "fluid conduit" refers to any tubular device, graft, and the like that may be implanted or otherwise introduced into a patient's body, e.g., catheters or grafts for dialysis access, peritoneal dialysis access, Foley catheters, nephrostomy tubes, endotracheal tubes, nasogastric tubes, and the like. The fluid conduit may be sized for introduction into an existing or created body lumen, e.g., within a patient's urinary tract, cardiovascular system, biliary system, and the like, and may include a lumen for conducting fluid therealong, e.g., urine, blood, bile, normal saline, lactated ringer's solution, and the like.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1A:
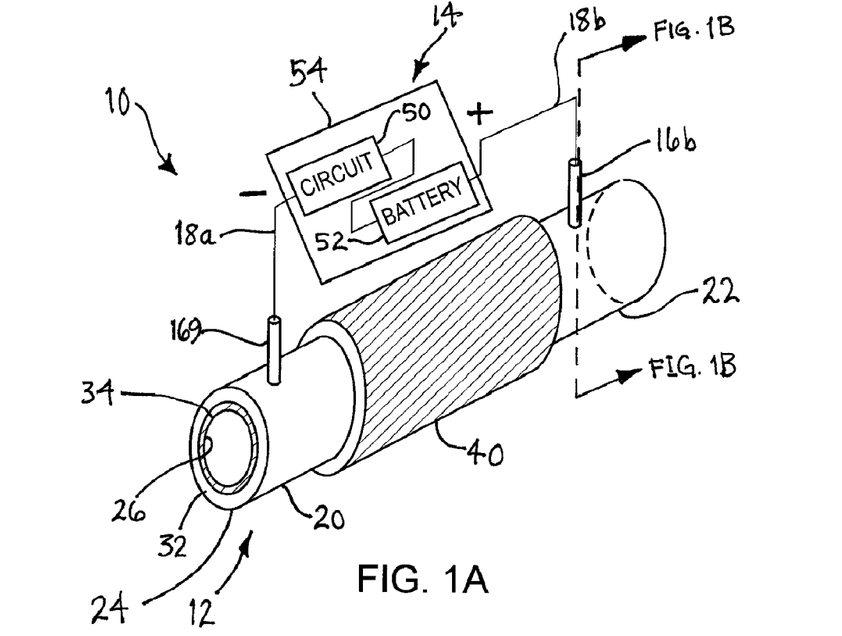
FIG. 1A is a perspective view of a first embodiment of an implantable medical device, including a vascular graft and a power source coupled to a portion of the graft.
Figure 1B:
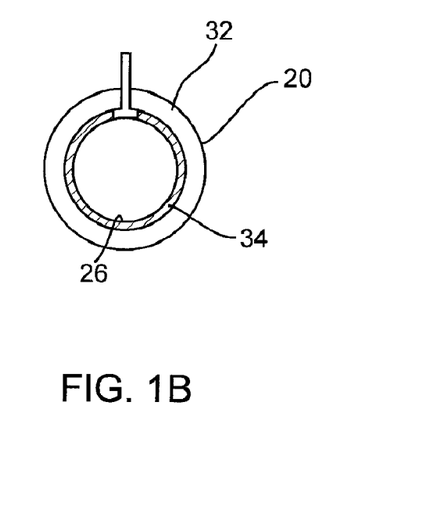
FIG. 1B is a cross-sectional view of the graft of FIG. 1A, taken along line 1B-1B.

Turning to the drawings, FIGS. 1A-1B show an exemplary embodiment of a medical device 10 that may be implanted within a body, e.g., for resisting thrombosis, infection and/or undesired tissue growth. As shown, the device 10 generally includes an elongate tubular member 12 and a power or voltage source 14, and may be suitable as a vascular graft, e.g., to provide a prosthetic coronary artery bypass graft connected between other vessels or body lumens, to replace a segment of a vessel or body lumen, or to be implanted within a vessel or body lumen (not shown).

Generally, the tubular member 20 includes a proximal end 22, a distal end 24, and a lumen 26 defined by an inner surface 28 extending between the proximal and distal ends 22, 24. In exemplary embodiments, the tubular member 20 may have a diameter or other cross-section between about one and six millimeters (1-6 mm), and a length between about fifty and five hundred millimeters (50-500 mm) At least a portion of the tubular member 20 is at least partially electrically conductive, e.g., for maintaining an electrical charge on at least the portion for an extended period of time, as described further below.

For example, as best seen in FIG. 1B, the tubular member 20 may include one or more layers, e.g., a base layer 32 and an at least partially conductive layer 34. The base layer 32 may be formed from fabric or other woven tubular material, such as Dacron, a polymeric or other plastic tube, such as expanded PTFE, or other material, similar to conventional grafts. Optionally, the proximal and/or distal ends 22, 24 may include one or more features, e.g., connectors and the like (not shown) for facilitating implantation of the tubular member 20. For example, the proximal and/or distal ends 22, 24 may include connectors (not shown) for creating an anastomosis between the ends 22, 24 and other body lumens, stents (also not shown) for securing the ends 22, 24 within a body lumen, and the like.

Unlike conventional grafts, the tubular member 20 includes an at least partially conductive layer 34, which in the embodiment shown in FIGS. 1A and 1B is disposed on an interior of the tubular member 20, i.e., exposed along the lumen 26. The conductive layer 34 may extend along the entire length of the tubular member 20 or may be provided only at the proximal and/or distal ends 22, 24, depending upon the application. In addition or alternatively, the tubular member 20 may include an outer layer and/or an intermediate layer of an at least partially conductive material (not shown), similar to the conductive layer 34, as described further elsewhere herein.

The conductive layer 34 may be composed of any of one or more electrically conductive or semi-conductive materials. The conductive layer 34 may be bonded to or otherwise coated onto the base layer 32, i.e., within the lumen 26 of the tubular member 20. Alternatively, the conductive layer 34 may be applied to a mandrel, e.g., a rod or tube having a desired diameter for the lumen 26, and the base layer 32 may be applied around or otherwise over the conductive layer 34. Once the base layer 32 and conductive layer 34 are bonded or otherwise fixed to one another, the mandrel may be removed.

Optionally, other features may be applied to the structure before or after removal from the mandrel, e.g., connectors, electrodes, and the like, as described elsewhere herein. For example, one or more electrodes may be bonded or otherwise coupled to the conductive layer 34 either before or after applying the base layer 32 over the conductive layer 34.

The conductive layer 34 may be semi-conductive, i.e., may have sufficient resistance to prevent substantial current flow along and/or from the conductive layer, thereby maintaining a desired electrical charge, e.g., a slight negative charge, along the lumen 26 of the tubular member 20. In addition or alternatively, the conductive layer 34 may maintain a desired electrical charge just beneath one or more exposed surfaces of the tubular member 12, e.g., to act similar to a capacitor in maintaining a charge for an extended period of time without substantial current flow or leakage.

For example, the conductive layer 34 may be semi-conductive such that current "leaks" from the conductive layer 34, i.e., flows at a substantially slow rate, thereby maintaining a desired voltage on the inner surface 28 with minimal current and power consumption. In one exemplary embodiment, the conductive layer 34 may be a conductive polymer, such as Poly (3,4-Ethylenedioxythiophene)/poly (styrenesulfonate), e.g., having a thickness between about a few microns. In another exemplary embodiment, the conductive layer 34 may include a relatively thin layer of a silicone dispersion loaded with conductive particles (not shown). For example, the conductive particles may be silver particles, silver coated glass beads, or platinum coated carbon particles, e.g., between about one and seven microns (0.001-0.007 inch or 0.025-0.175 mm) in average diameter. In an alternative embodiment, an additional electrically insulating coating or layer (not shown) may be provided over the conductive layer 34. For example, the inner surface of the lumen 26 (and optionally the ends 22, 24) may be coated with a polymer or material that is not electrically conductive, such as silicone, polyurethane, or fluoropolymer, thereby limiting the conductivity of the entire inner surface and/or the most proximal and distal portions of the inner surface. The coating may be relatively thin, e.g., having a thickness between about 0.0001 and 0.1 millimeter (0.0001-0.1 mm), thereby reducing the conductivity while still allowing an electrical charge to be maintained on the desired portion(s) of the inner surface. In this alternative, more conductive materials may be used for the conductive layer 34, and the coating thickness may be adjusted to provide the desired level of conductivity.

In an alternative embodiment, the tubular member 20 may be formed from polymeric, plastic, or other base material including one or more conductive particles, such as carbon or those identified elsewhere herein, dispersed within the material. For example, the tubular member 20 may be formed from polyurethane, silicone rubber, or other non-electrically conductive material loaded with conductive particles. For example, a mixture of the desired base material and the conductive particles may be provided within an extruder, and the mixture may be extruded substantially continuously into a tubular shape, which may be cut or otherwise separated into one or more tubular members 20. Alternatively, the mixture may be placed within a mold, cast, or other device for forming the mixture into the tubular member 20.

In this alternative, one or more portions of the tubular member 20 may be coated with an electrically insulating layer, e.g., similar to the insulating layers described elsewhere herein. For example, the outer surface and/or end surfaces of the tubular member 20 may be coated, e.g., to prevent electrical leakage from these surfaces and/or to apply the desired charge only to the inner surface 28.

In addition, as shown in FIG. 1A, one or more electrodes 16 may be provided on the tubular member 20. For example, as shown, an electrode 16 may be provided on each of the proximal and distal ends 22, 24 of the tubular member 20. The electrodes 16 may extend transversely from the tubular member 20, e.g., through the base layer 32 to electrically couple the electrodes 16 to respective ends of the conductive layer 34. Alternatively, the electrodes 16 may be conductive regions (not shown) applied or otherwise formed on the exterior of the proximal and distal ends 22, 24, e.g., for endoluminal applications.

The electrodes 16 may be coated, covered, or otherwise electrically insulated to prevent current flow, e.g., from the electrodes 16 to tissue, fluid, or other areas adjacent the electrodes 16 and/or outside the tubular member 20. One or more wires or other electrical leads 18 may be coupled to the electrodes 16, e.g., by soldering, bonding, fusing, and the like, which may extend from the tubular member 12, e.g., to the power source 14. Alternatively, the leads 18 may be formed from silicone integrated with silver particles, similar to other material described herein. In another alternative, the leads 18 may be formed from a conductive epoxy, such as CW2400 (Chemtronics®).

Optionally, the leads 18 may be coupled directly to the conductive portion 34 of the tubular member 20, e.g., through the base layer 32. The leads 18 may be simply insulated electrical wires compatible with being implanted within a patient's body, e.g., to extend along one or more body lumens, through body cavities, and/or tissue, as described elsewhere herein.

With continued reference to FIG. 1A, the power source 14 generally includes a circuit 50 and a battery or other storage device 52, e.g., provided within a casing 54. The casing 54 may have a size and/or shape to facilitate implantation within a patient's body, e.g., subcutaneously or deep within the body, as described further elsewhere herein.

The battery 52 may be a single use device, e.g., that may be replaced after being depleted, or may be rechargeable, e.g., using a source (not shown) outside a patient's body. In an exemplary embodiment, the battery 52 may be a direct current (DC) voltage source. The circuit 50 may be any number of resistive or active elements to control the flow of electrical current from the battery 52, e.g., to the tubular member 12. In exemplary embodiments, the circuit 50 may be an inverting operational amplifier or a simple voltage divider circuit. In yet another embodiment, the power source 14 may simply include a battery, and the circuit 50 may be omitted. Additionally, the circuit may include the battery in series with a resistor also in series with the conductive surface of the device, which is then in series through the tissues of the patient, completing the circuit back to the battery.

Optionally, the power source 14 may include a switch (not shown) for activating and/or deactivating the power source 14. For example, if the power source 14 is implanted subcutaneously beneath a patient's skin, a switch may be provided on the casing 54 that may be selectively actuated by pressing on the skin above the casing 54. In addition or alternatively, the power source 14 may include a telemetry device, e.g., a transmitter and/or receiver, for communicating to locations external to the patient's body. For example, the telemetry device may include a radio frequency, acoustic, inductive, or other transceiver that may communicate through intervening tissue within an external device. Such a telemetry device may be used to activate and/or deactivate the power source 14, to recharge the battery 50, and/or for other communications, as is known in the art.

The power source 14 may be implanted in relatively close proximity to the tubular member 12, e.g., within a body lumen or cavity adjacent the tubular member 12. Optionally, the power source 14 may be mounted directly on or to the tubular member 12. Alternatively, the power source 14 may be implanted remotely from the tubular member 12, e.g., subcutaneously, and the lead(s) 18 may extend between the power source 14 and the tubular member 12.

The power source 14 may be electrically coupled to the tubular member 12, e.g., via leads 18, such that a negative charge is imparted to the conductive layer 34. The imparted negative charge may repel negatively charged blood cells and/or other cells, and or may inhibit the intrinsic and or extrinsic pathways of the clotting cascade e.g., to reduce the risk of thrombosis, infection, or undesired tissue growth within the lumen 26 of the tubular member 12. In addition or alternatively, the power source 14 may be configured to impart a negative charge to another conductive layer (not shown), e.g., on or adjacent the outer surface of the tubular member 12. The power source 14 may be configured to simultaneously, alternatively, or separately impart a negative charge to the conductive layer 34 and other conductive layer(s). In yet another embodiment, the power source 14 may be coupled to the tubular member 12 such that a negative charge is imparted to the conductive layer 34, while a positive charge is imparted to another conductive layer (not shown), e.g., on the outer surface of the tubular member 12.

Alternatively, the power source 14 may be electrically coupled indirectly to the tubular member 12. For example, one lead 18 may extend from the power source 14 to the tubular member 12 and the other lead 18 may be coupled to an anatomical structure adjacent to the tubular member 12 or otherwise within the patient's body such that the anatomical structure (and any intervening structures, fluids, and then like) provides a conductive path to complete the circuit between the power source 14 and the tubular member 12. Alternatively, at least a portion of the casing 54 may be coupled to the positive terminal of the battery 50 to provide a positive charge on the casing 54, which may create a circuit partially through the patient's body with the negatively charged portion of the tubular member 12. The tubular member 12 may be coupled to the negative terminal of the battery 50, e.g., by a single lead 18.

Figure 2:
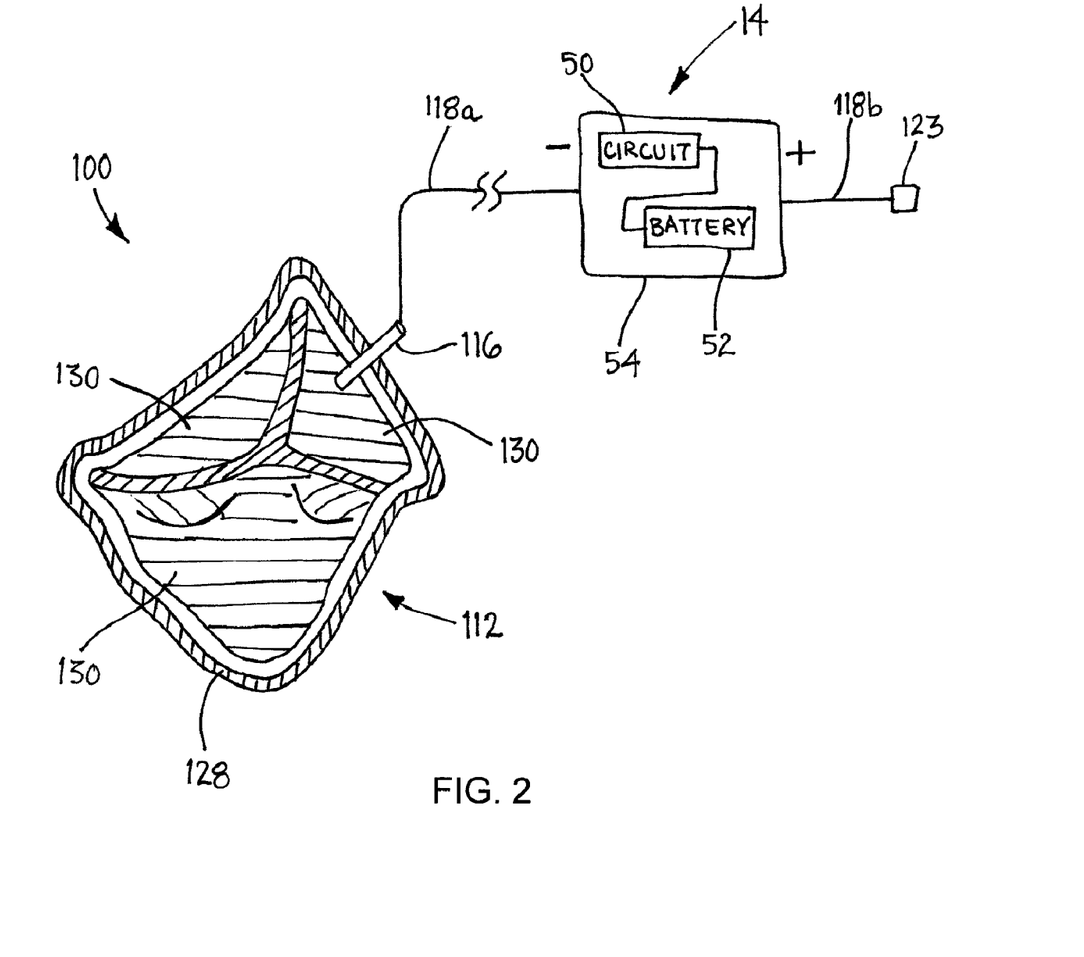
FIG. 2 is a perspective view of another embodiment of an implantable medical device, including a heart valve assembly and a power source coupled to a portion of the heart valve assembly.

Turning to FIG. 2, another embodiment of an implantable medical assembly 100 is shown that includes a mechanical heart valve 112 and a power source 14, which may be similar to the embodiments described above. Generally, the heart valve 112 includes a frame 128, e.g., having a circular or other annular shape and one or more valve elements 130 connected to the frame 128 such that the valve elements 130 may open and close, similar to conventional heart valves.

The components of the heart valve 112 may be formed from conventional materials, e.g., such as pyrolytic carbon, or conductive or semi-conductive materials, similar to other embodiments described herein. In one embodiment, the frame 128 and valve elements 130 of the heart valve 112 may be formed a rigid or semi-rigid material, such as pyrolytic carbon. Unlike conventional valves, one or more outer surfaces of the valve elements 130 and/or other surfaces of the heart valve 112, e.g., that may be exposed to blood flow, may be coated with an at least partially conductive layer (not shown), such as those described elsewhere herein. For example, the conductive layer may be bonded to or otherwise cover the valve elements 130 to provide a desired voltage and/or current leakage from the valve elements 130.

In an exemplary embodiment, the conductive layer may include a polymer, such as Poly(3,4-Ethylenedioxythiophene)/poly(styrenesulfonate), or a monomer, such as 3,4-Ethylenedioxythiophene, which may be polymerized by adding Ferric Toluene Sulfonate as an oxidant. In yet another embodiment, the valve elements 130 may be coated with a polymer loaded with conductive particles, such as silver particles as described elsewhere herein. Alternatively, the valve elements 130 may be formed from electrically conductive material, such as stainless steel. In this alternative, the valve elements may be coated with a polymer or other material to reduce the conductivity of the material, similar to other embodiments described elsewhere herein.

One or more electrodes 116 may be coupled to a portion of the heart valve 112, e.g., to the frame 128 and/or valve elements 130, and the power source 14 may be coupled to the heart valve 112 via one or more leads 118. For example, as shown in FIG. 2, an electrode 116 is coupled to the valve elements 130 (e.g., to the semi-conductive coating and/or underlying conductive material), and an electrical lead 118 extends from the electrode 116 to the power source 14. The power source 14 may be similar to the previous embodiments, e.g., configured to impart a negative charge to the valve elements 130. For example, the lead 118a may be coupled to the negative terminal of the battery 50, and another lead 118b may extend from the power source 14, e.g., coupled to the positive terminal of the battery 50, to an electric pad 123, which may be coupled to an anatomical structure within the patient's body. Thus, the resulting circuit may include an electrical path through the patient's body from the electric pad 123 to the valve elements 130.

The heart valve 112 may be implanted within a patient's heart, e.g., to replace an existing natural or prosthetic valve, using known procedures, and the power source 14 may be implanted at another location, e.g., subcutaneously, with the lead 118a extending from the power source 14 through the patient's body to the electrode 116.

The negative charge may be maintained substantially constant for an extended period of time, e.g., at a voltage between about zero (0) and −0.5 volts. For example, depending upon the life of the battery 54, the power source 14 may maintain the negative charge constantly for the life of the implant, e.g., up to several decades, or may only intermittently apply the negative charge to the surface of the implanted device. The imparted negative charge may repel negatively charge blood cells and/or other negatively charged cells in the blood, e.g., may inhibit the intrinsic and or extrinsic coagulation pathways to prevent blood from coagulating on the surfaces of the valve elements 130, which may obviate the need to take oral anticoagulants and/or reduce the risk of hemorrhage.

In another embodiment, the power source 114 may be configured to impart a negative charge to a conductive layer (not shown) under an outer surface of the valve elements 130, e.g., such that the valve elements 130 behave similar to a capacitor maintaining a negative charge for an indefinite period of time. Thus, the power source 14 may deliver a relatively low negative voltage at the surfaces of the valve elements 130, e.g., such that a small current (e.g., between about zero and five milliamps per square centimeter (0-5 mA/cm2) flows at the surfaces. This relatively small current may increase coagulation resistance by as much as four hundred percent (400%).

Figure 3A:
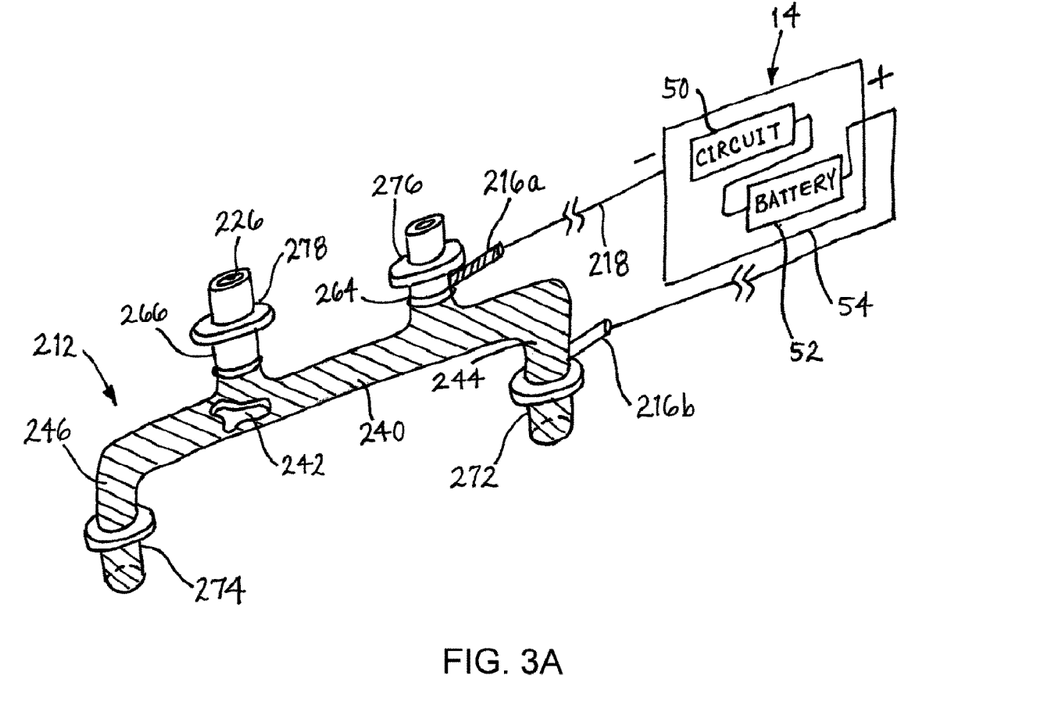
FIGS. 3A and 3B are perspective and cross-sectional views, respectively, of yet another embodiment of an implantable medical device, including an arteriovenous hemodialysis access graft and a power source coupled to a portion of the access graft.
Figure 3B:
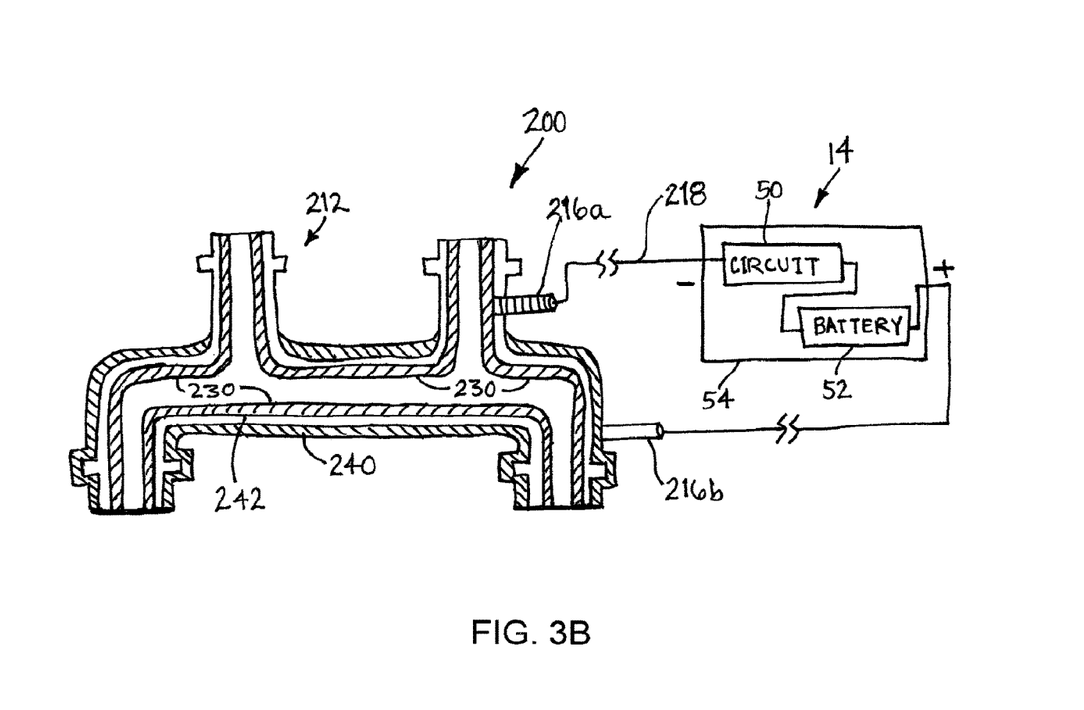

Turning to FIGS. 3A-3B, still another embodiment of an implantable medical apparatus 200 is shown that generally includes a vascular graft, e.g., an arteriovenous hemodialysis access graft 212, and a power source 214. In addition, one or more electrode elements 216 and/or leads 218 may be provided, e.g., which may be secured or otherwise coupled to the access graft 212, similar to the previous embodiments.

The access graft 212 generally includes a main cylindrical body 242 in fluid communication with graft tubes 244, 246 and access tubes 264, 266 via lumen 226. The cylindrical body 242 may include any material suitable for implantation within the human body, such as expanded PTFE. The exterior surface of the cylindrical body 242 as well as the exterior of the graft tubes 244, 246 may be coated with an outer conductive layer 240. The outer conductive layer 240 may include a conductive material, such as the polymers or monomers described elsewhere herein. The interior surface of the cylindrical body 242 as well as the interior of the graft tubes 244, 246 and the interior of the access tubes 264, 266 may also be coated with an inner conductive layer 230. The inner conductive layer 230 may also include a conductive material similar to those described elsewhere herein.

The graft tubes 244, 246 may include fittings 272, 274 that are suitable for securing to desired locations within a patient's body, e.g., to a vein, artery, or other body lumen. The access tubes 264, 266 may include connectors 276, 278 suitable for securing to complimentary connectors (not shown) of a dialysis machine (not shown). The connectors 276, 278 may include any type of seals or valves known to a person of ordinary skill in the art.

One or more electrodes 216 may be provided that are coupled to the inner and/or outer conductive layers 230, 240. For example, as shown, an electrode 216a is coupled to the inner conductive layer 230, and an electrode 216b is coupled to the outer conductive layer 240.

The power source 14 generally includes a circuit 50 and a battery 52 within a casing 54, similar to other embodiments described herein. For example, the battery 52 may be a nonrechargeable or rechargeable direct current source with an operating voltage in the range of about −9 volts to +9 volts, e.g., between about −0.5 and +0.5 volts, and the circuit 50 may be any number of resistive or active elements for controlling flow of electrical current from the battery 52.

The power source 14 may be electrically coupled to the electrode 216a via a negative lead 218 and to the electrode 216b via a positive lead 219. The leads 218, 219 may include one or more wires or other conducts, similar to other embodiments described herein. For example, the power source 14 may be coupled to the access graft 212 such that a negative charge is imparted to the inner conductive layer 230. The imparted negative charge may repel negatively charge blood cells and/or other cells and/or may inhibit the intrinsic and/or extrinsic coagulation pathways, e.g., to reduce the risk of thrombosis within the implantable access graft 212. In an opposite manner, the power source 14 may be coupled to the access graft 212 such that a positive charge is imparted to the outer conductive layer 240. The imparted positive charge may preferentially increase coagulation and/or smooth muscle cell proliferation to the outer surface, which may improve sealing and/or scarring of the implantable access graft 212 in position. Alternatively, the power source 14 may be configured to apply a positive charge to the casing 54d outer surface, which may impart a positive charge to the outer conductive layer 240 via electrical flow through the patient's body.

Figure 4A:
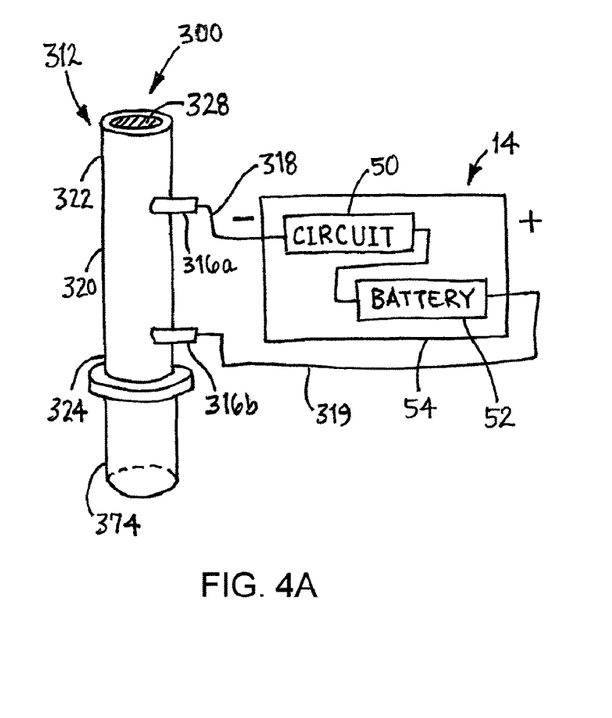
FIGS. 4A and 4B are perspective and cross-sectional views, respectively, of still another embodiment of an implantable medical device, including an implantable blind-ended tubular graft and a power source coupled to a portion of the graft.
Figure 4B:
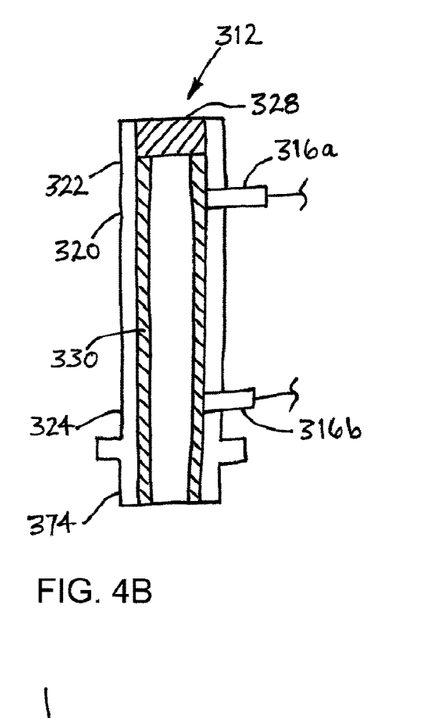

Turning to FIGS. 4A-4B, yet another embodiment of an implantable medical apparatus 300 is shown that generally includes a vascular graft in the form of an implantable blind-ended graft member 312 and a power source 14. In addition, electrodes 316a, 316b may also be provided, which are coupled to the graft member 312. The graft member 312 may be electrically coupled to the power source 14 via a negative lead 318 and a positive lead 319.

The blind-ended graft member 312 may include an elongate tubular member 320 having a proximal end 322 and a distal end 324, with a graft fitting 374 attached to the distal end 324, and a septum 328 on the proximal end 322. As best seen in FIG. 4B, the graft member 312 may also include a conductive layer 330 on an inner surface thereof, e.g., coupled to the electrodes 316a, 316b.

The tubular member 320 may be formed from one or more materials suitable for implantation within a patient's body, such as expanded PTFE or silicone dispersion integrated with silver particles, carbon particles, or other electrically conductive material similar to other embodiments described herein. The graft fitting 374 may be formed from suitable material for securing to the vasculature of a patient using known methods, such as suturing. In an alternative embodiment, the graft fitting 374 may include an outer conductive layer (not shown) that is in electrical communication with the inner conductive layer 330. A negative charge may then be imparted to the outer conductive layer (not shown) when a negative charge is imparted to the inner conductive layer 330, e.g., as describe below.

The inner conductive layer 330 may include a polymer, such as Poly(3,4-Ethylenedioxythiophene)/poly(styrenesulfonate) or a monomer such as 3,4-Ethylenedioxythiophene, which may be polymerized by adding Ferric Toluene Sulfonate as an oxidant. In another embodiment, the inner conductive layer 330 may include a relatively thin layer of a silicone dispersion loaded with conductive particles (not shown), e.g., as described elsewhere herein.

The electrodes 316a, 316b may be coupled to the inner conductive layer 330, e.g., at proximal and distal ends 322, 324 of the tubular member 320. The septum 328 may include any suitable material that is resilient and self sealing, e.g., that may be punctured with a needle a automatically reseal upon removal of the needle.

The power source 14 may be coupled to the graft member 312 such that a negative charge is imparted to the inner conductive layer 330. The imparted negative charge may act to repel negatively charge blood cells and other cells from the inner lumen of the graft member 312 and/or reduce thrombosis therein by inhibiting the intrinsic and/or extrinsic coagulation pathways.

Figure 4C:
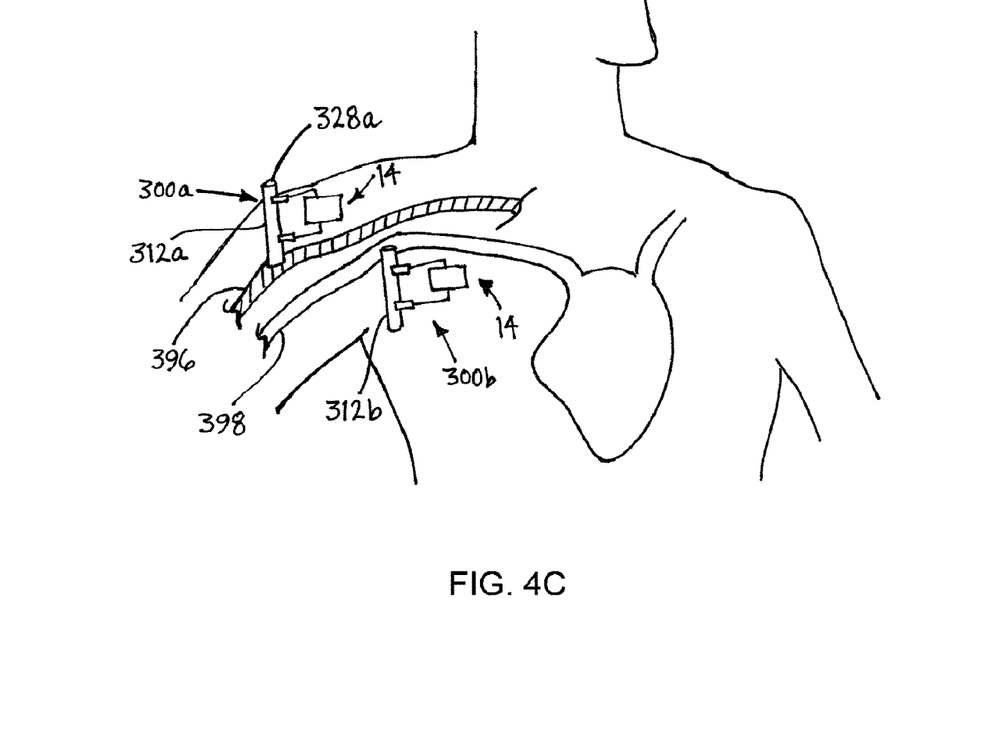
FIG. 4C is a partial cross-sectional view of a body, showing a pair of implanted blind-ended tubular grafts, such as that shown in FIGS. 4A-4B, implanted within the body.

During use, as shown in FIG. 4C, a pair of apparatus 300a, 300b (each similar to apparatus 300 of FIGS. 4A and 4B) may be implanted within a patient's body. For example, apparatus 300a may be implanted, e.g., by sewing into an artery 396, and apparatus 300b may be implanted, e.g., by sewing into a vein 398. The apparatus 300a, 300b may preclude blood flow at all times except during hemodialysis, i.e., when needles, cannulas, or other devices are used to penetrate the septums 328. Thus, blood flow with a hemodialysis machine or other device (not shown) may be established via the apparatus 300a, 300b by accessing each graft member 312a, 312b via septum 328a, 328b.

Figure 5:
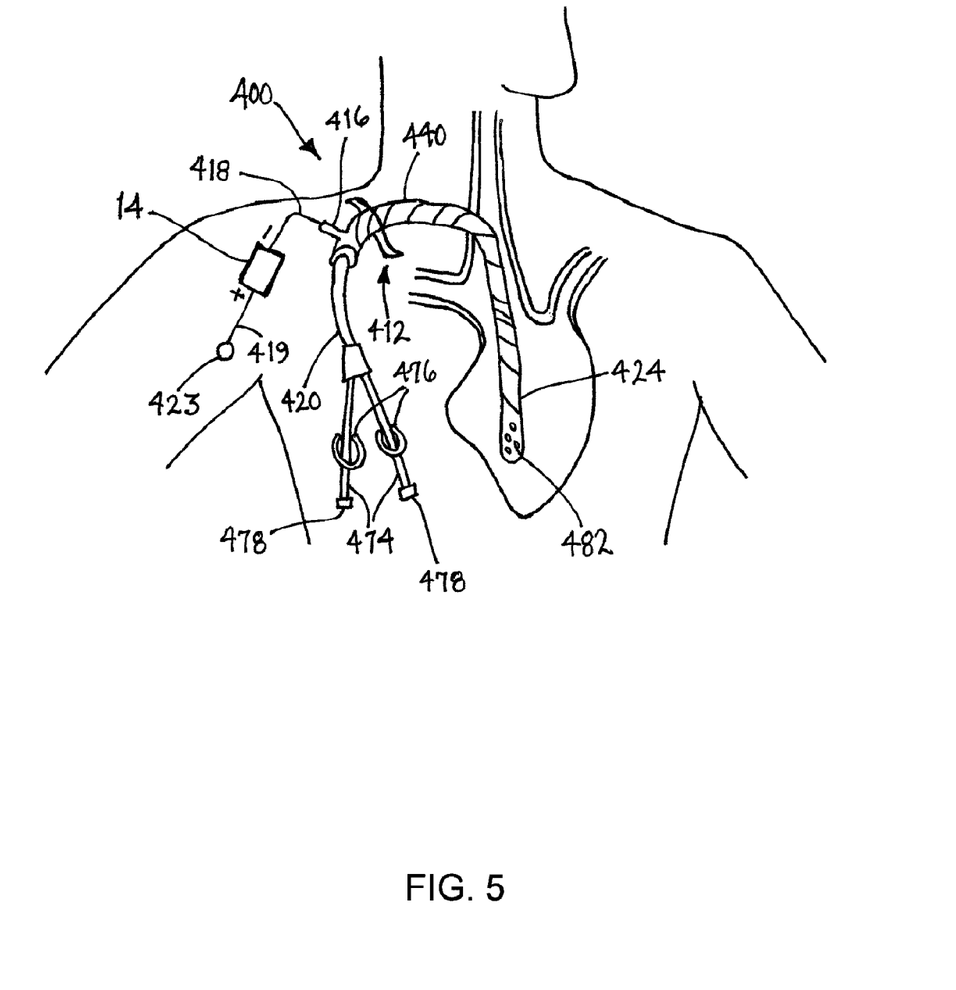
FIG. 5 is a partial cross-sectional view of a body, showing another embodiment of an implanted medical device, including a dialysis catheter and a power source, implanted within the body.

Turning to FIG. 5, still another embodiment of an implantable medical apparatus 400 is shown that generally includes an implantable dialysis catheter 412 and a power source 14. In addition, an electrode 416 may be provided, which may be coupled to the dialysis catheter 412, and the dialysis catheter 412 may be coupled to the power source 14 via a negative lead 418. The apparatus 400 may also include a positive lead 419 attached to an electric pad 423, e.g., similar to other embodiments described herein.

The dialysis catheter 412 generally includes an elongate tubular member 420 including a proximal end 422 and a distal end 424, and a hemodialysis connection assembly 470. The tubular member 420 may also include a plurality of inlet ports 482, e.g., on the distal end 424. The tubular member 420 may be formed from a substantially flexible or semi-rigid material, such as expanded PTFE, and a substantial portion of an outer surface of the tubular member 420 may be coated with an at least partially electrically conductive layer 440, similar to other embodiments described herein.

The hemodialysis connection assembly 470 generally may include a pair of access stems 474, as well as a pair of flow clamps 476 and a pair of dialysis connectors 478. The construction of the connection assembly 470 is with any number of materials and methods known to a person of ordinary skill in the art.

The power source 14 is similar to those described elsewhere herein, e.g., including a battery or other energy source, and/or one or more circuits (not shown) for controlling electrical flow from the battery. The power source 14 may be coupled to the dialysis catheter via lead 418 and to an electric pad 423 coupled to an anatomical structure within the patient's body. The power source 14 may be configured to impart a negative charge to the conductive outer layer 440, e.g., at a substantially constant voltage between about zero (0) and −0.5 volts. Alternatively, if the outer surface of the tubular member 420 includes a conductor, the power source 14 may be configured to deliver a low negative voltage at the outer surface such that a small current, approximately between about zero and five (0-5) 5.0 milli-amps/cm2, flows at the surface. In another alternative, the negative charge may be imparted to the surface of the tubular member 420 by using an electrically polarized conductor (not shown) disposed below the surface of the tubular member 420 instead of coating the elongate cylinder 420 with the conductive outer layer 440, similar to other embodiments described herein.

FIG. 5 shows the dialysis catheter 412 being used as a "subclavian line" because of the catheters 412 anatomical location in the subclavian artery. It may be appreciated that the catheter 412 may be easily modified for use as a "femoral line," as a peritoneal dialysis catheter, or in other locations within a patient's body.

Figure 6:
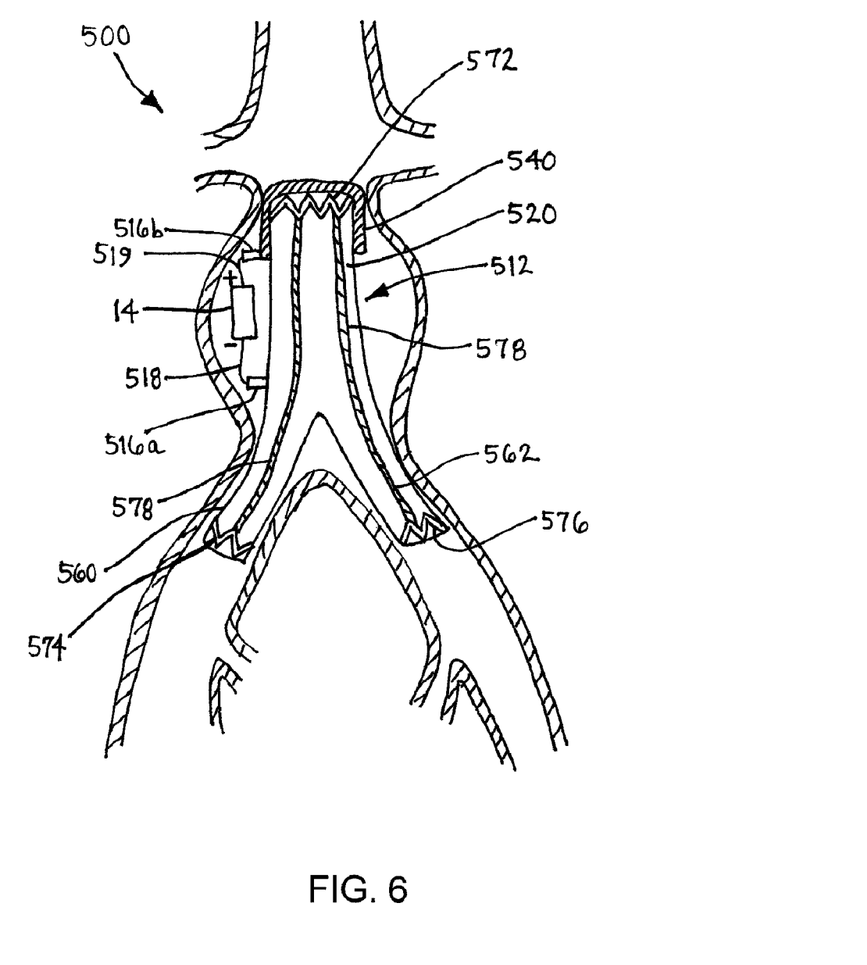
FIG. 6 is a cross-sectional view of a body, showing yet another embodiment of an implantable medical device, including an endovascular aortic aneurysm repair graft and a power source, implanted within the body.

Turning to FIG. 6, another embodiment of an implantable medical apparatus 500 is shown that generally includes an implantable endovascular aortic aneurysm graft 512 and a power source 14. In addition, electrodes 516a, 516b may also be provided, which are coupled to the aortic graft 512. The aortic graft 512 may be coupled to the power source 514 via a negative and a positive lead 518, 519 and electrodes 516a, 516b, respectively.

The aortic graft 512 generally includes a main body or tubular member 520 integrated with a first branch member 560 and second branch member 562. The aortic graft 512 further includes a proximal stent 572 on the main body 520 and a first and second distal stent 574, 576 on the first and second branch members 560, 562, respectively. The aortic graft 512 may also include a plurality of electric conductors 578 facilitating an electrical connection between the proximal stent 572 and the first and second distal stent 574, 576.

The aortic graft 512 may be formed from any number of materials suitable for implantation and/or providing desired strength and/or durability. In one embodiment, the aortic graft 512 may be formed from a woven or fabric material, such as nylon, polypropylene, or other polymer, or expanded PTFE or other extruded polymers.

Optionally, the main body 520 may include an outer conductive layer 540 including an at least partially electrically conductive material, similar to those described elsewhere herein. The outer conductive layer 540 may facilitate improvement of an electrically charged area adjacent the proximal stent 572. The electrode 516b may be attached to the outer conductive layer 540, or, alternatively, may be attached to the proximal stent 572. The electrode 516a may be coupled to the outer surface of the main body 520, or, alternatively, to an electric pad (not shown) coupled to an anatomical structure within the patient's body, such as a segment of the patient's vasculature, to complete the circuit.

The proximal stent 572 and the first and second distal stent 574, 576 may be formed from suitable materials, e.g., to provide self-expanding or balloon-expandable stents, e.g., such that the aortic graft 512 may be implanted using one or more catheters (not shown). If the stent material is not inherently electrically conductive, the outer surface of the stent material may be coated with a suitable conductive material, similar to the embodiments described elsewhere herein.

The power source 14, which may be similar to those described elsewhere herein, may be coupled to the aortic graft 512 such that a positive charge is imparted to the outer conductive layer 540, the proximal stent 572, and/or the first and second distal stents 574, 576. The positive charge may be maintained substantially constant, e.g., between about zero (0) and +0.5 volts. The imparted positive charge may increase thrombosis or smooth muscle proliferation particularly surround the proximal stent 572, which is a common failure site for aortic repairs. Thus, the apparatus 500 may substantially reduce the risk of endoleaks that may otherwise occur after implantation.

Figure 7:
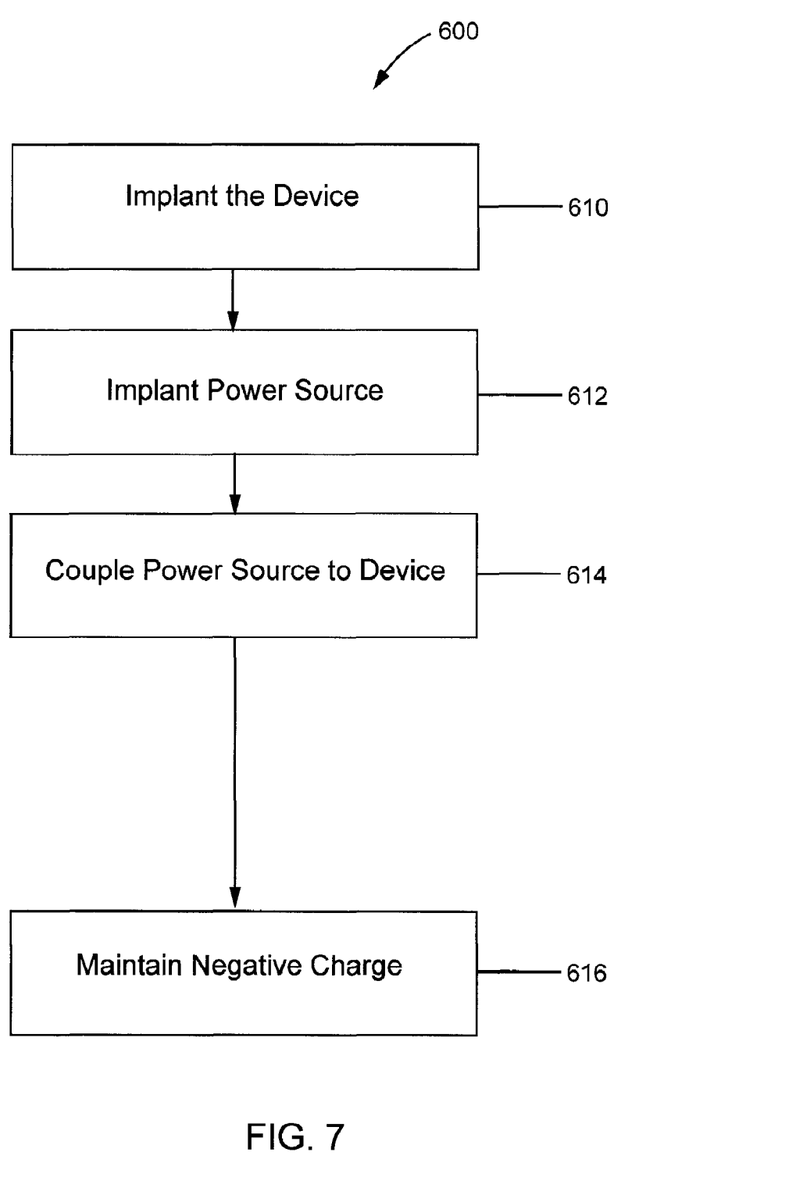
FIG. 7 is a flowchart showing an exemplary method for implanting a medical device for preventing thrombosis on the implantable device.

Turning to FIG. 7, a flowchart 600 is shown that illustrates an exemplary method for delivering an implantable device within a body to prevent thrombosis, infection, and/or undesired tissue growth. Although the steps are described in an exemplary order, it will be appreciated that the order of the steps may be modified and/or one or more of the steps may be omitted. At step 610, a device may be implanted within a patient's body, the device including an at least partially electrically conductive portion. For example, as described above, the device may include a vascular graft, a prosthetic heart valve, a hemodialysis catheter, and the like, which may be implanted within or coupled to the patient's vasculature or other location.

At step 612, a power source may be implanted within the patient's body. For example, the power source may be implanted subcutaneously, e.g., by creating an incision and implanting the power source beneath the patient's skin at an accessible location. At step 614, the power source may be coupled to the device, e.g., by connecting one or more leads between the power source and the device. Optionally, this may include coupling the power source to an anatomical location within the patient's body, e.g., thereby using the patient's body to complete a circuit between the power source and the device. At step 616, a negative electrical charge may be applied to the at least partially electrically conductive portion, e.g., for an indefinite time to prevent thrombosis, infection, and/or undesired tissue growth, for example by resisting cells from adhering to the at least partially conductive portion.

The power source, e.g., including a battery or other energy source may be configured to maintain a substantially constant electric charge to the at least partially electrically conductive portion, e.g., between about zero (0) and −0.5 volts, for an indefinite period of time. For example, when the power source has depleted, it may be replaced, e.g., by reaccessing the subcutaneous location and replacing the battery. Alternatively, the power source may be recharged, e.g., using an external device that may communicate with the power source using wireless telemetry, as described above. The power source may remain on substantially continuously, or may periodically turn on for a predetermined time, depending upon the application and the desired reduction in cell adhesion.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. An implantable medical system, comprising:
   an implantable medical device comprising an elongate tubular member sized for implantation at least partially within a patient's body, the device comprising an at least partially electrically conductive portion that is disposed within a patient's body upon implantation; and
   a power source coupled to the at least partially electrically conductive portion by one or more leads such that a small DC electric current flows to the at least partially electrically conductive portion substantially continuously to maintain a substantially constant charge for the life of the implantable medical device.

2. The system of claim 1, wherein the power source is configured to provide a negative electric charge at least part of the time to the at least partially electrically conductive portion that is between 0 and —0.5 volts.

3. The system of claim 1, wherein the power source is configured for maintaining a negative charge on the at least partially electrically conductive portion for repelling negatively charged cells from the at least partially electrically conductive portion.

4. The system of claim 1, wherein the power source comprises a battery and a circuit for controlling the substantially continuous flow of the small DC current from the battery to the at least partially conductive portion.

5. The system of claim 4, wherein the circuit comprises one of an inverting operational amplifier and a voltage divider.

6. The system of claim 1, wherein the at least partially electrically conductive portion comprises a charged conductor disposed below exposed surfaces of the medical device, wherein the charged conductor is configured to electrically polarize the surface of the medical device.

7. The system of claim 1, wherein the at least partially electrically conductive portion comprises a conductive surface of the implantable medical device.

8. The system of claim 1, wherein the at least partially electrically conductive portion comprises a semi-conductive surface of the implantable medical device configured to cause current to flow from the power source to the semi-conductive surface, thereby maintaining a desired voltage on the device.

9. The system of claim 1, wherein the tubular member comprises a vascular graft, and wherein the vascular graft comprises proximal and distal ends and an at least partially electrically conductive layer coating at least one of the distal and proximal ends.

10. The system of claim 1, wherein the at least partially electrically conductive portion comprises a conductive layer applied to an external surface of the tubular member.

11. The system of claim 1, wherein the at least partially electrically conductive portion comprises a polymer.

12. The system of claim 1, wherein the tubular member comprises a catheter.

13. The system of claim 1, wherein the power source is configured to deliver a voltage such that a small current that is greater than zero and not more than five milliamps/cm2 flows to the at least partially electrically conductive portion.

14. The system of claim 1, wherein the power source is configured to provide the small DC current to maintain the charge for the life of the implantable medical device.

15. An implantable medical apparatus, comprising:
    an implantable vascular graft comprising an elongate tubular member including proximal and distal ends and an at least partially electrically conductive portion;
    an electrode coupled directly to the at least partially electrically conductive portion; and
    a direct current (DC) power source coupled to the electrode for providing an electric current to flow to the at least partially electrically conductive portion, thereby maintaining a desired voltage on the graft for the life of the graft.

16. The medical apparatus of claim 15, wherein the vascular graft comprises PTFE material.

17. The medical apparatus of claim 15, wherein the vascular graft comprises a polymer material integrated with conductive particles, thereby providing the at least partially electrically conductive portion.

18. The medical apparatus of claim 15, wherein the at least partially electrically conductive portion comprises a polymer.

19. The medical apparatus of claim 15, wherein the at least partially electrically conductive portion comprises a conductive layer applied to an internal surface of the tubular member.

20. The medical apparatus of claim 19, wherein the at least partially electrically conductive portion further comprises a conductive layer applied to an external surface of the tubular member.

21. The medical apparatus of claim 20, wherein the power source is coupled to the tubular member to create a negative charge on the internal surface and a positive charge on the external surface.

22. The medical apparatus of claim 15, wherein the at least partially electrically conductive portion comprises semi-conductive material.

23. A vascular graft, comprising:
a tubular member comprising a luminal surface, at least a portion of the luminal surface being electrically conductive; and
means for applying an electrical current comprising a direct current (DC) voltage source directly coupled to the luminal surface of the graft such that a small current flows from the voltage source to the luminal surface, thereby maintaining a desired voltage on the luminal surface for the life of the tubular member.

* * * * *